United States Patent
Berg

[11] Patent Number: 5,993,610
[45] Date of Patent: Nov. 30, 1999

[54] SEPARATION OF ETHYL ACETATE FROM ETHANOL BY AZEOTROPIC DISTILLATION

[76] Inventor: Lloyd Berg, 1314 S. 3rd Ave., Bozeman, Mont. 59715

[21] Appl. No.: 09/072,008

[22] Filed: May 4, 1998

[51] Int. Cl.$^6$ .............................. B01D 3/36; C07C 67/48; C07C 29/82
[52] U.S. Cl. ................................. 203/57; 203/60; 203/62; 203/63; 203/68; 203/69; 203/70; 560/248; 568/913
[58] Field of Search ................................... 203/60, 57, 68, 203/70, 69, 63, 62; 568/913, 890; 560/248

[56] References Cited

U.S. PATENT DOCUMENTS

| | | | |
|---|---|---|---|
| 1,873,005 | 8/1932 | Merley | 203/18 |
| 2,050,513 | 8/1936 | Van Peski et al. | 203/18 |
| 2,640,017 | 5/1953 | Graff | 203/99 |
| 4,256,541 | 3/1981 | Muller et al. | 203/19 |
| 4,379,028 | 4/1983 | Berg et al. | 203/57 |
| 4,473,444 | 9/1984 | Feldman et al. | 203/69 |
| 4,549,938 | 10/1985 | Berg et al. | 203/58 |
| 4,569,726 | 2/1986 | Berg et al. | 203/60 |
| 4,582,570 | 4/1986 | Mix | 203/63 |
| 4,645,569 | 2/1987 | Akabane et al. | 203/19 |
| 4,690,734 | 9/1987 | Berg et al. | 203/64 |
| 4,695,350 | 9/1987 | Berg | 203/60 |
| 4,718,988 | 1/1988 | Berg et al. | 560/248 |
| 4,724,049 | 2/1988 | Berg et al. | 560/248 |
| 5,449,440 | 9/1995 | Rescalli et al. | 568/913 |

*Primary Examiner*—Virginia Manoharan

[57] ABSTRACT

Ethyl acetate cannot be separated from ethanol by distillation or rectification because of the closeness of their boiling points. Ethyl acetate is readily separated from ethanol by azeotropic distillation. Effective agents are ethyl ether, methyl formate and cyclohexane.

1 Claim, No Drawings

SEPARATION OF ETHYL ACETATE FROM ETHANOL BY AZEOTROPIC DISTILLATION

FIELD OF THE INVENTION

This invention relates to a method for separating ethyl acetate from ethanol using certain organic liquids as the agent in azeotropic distillation.

DESCRIPTION OF PRIOR ART

Azeotropic distillation is the method of separating close boiling compounds or azeotroped from each other by carrying out the distillation in a multiplate rectification column in the presence of an added liquid, said liquid forming an azeotrope with one or more of the compounds to be separated. Its presence on each plate of the rectification column alters the relative volatility in a direction to make the separation on each plate greater and thus require either fewer plates to effect the same separation or make possible a greater degree of separation with the same number of plates. The azeotrope forming agent is introduced with the feed to a continuous column. The azeotrope forming agent and the more volatile component are taken off as overhead product and the less volatile component comes off as bottoms product. The usual methods of separating the azeotrope former from the more volatile component are cooling and phase separation or solvent extraction.

The usual method of evaluating the effectiveness of azeotropic distillation agents is the change in relative volatility of the compounds to be separated. Table 1 shows the degree of separation or purity obtainable by theoretical plates at several relative volatilities. Table 1 shows that a relative volatility of at least 1.2 is required to get an effective separation by rectification.

TABLE 1

Effect of Relative Volatility on Theoretical Stage Requirements.

| Separation Purity, | Relative Volatility | | | | | | | |
|---|---|---|---|---|---|---|---|---|
| Both Products (Mole Fraction) | 1.02 | 1.1 | 1.2 | 1.3 | 1.4 | 1.5 | 2.0 | 3.0 |
| | Theoretical Stages at Total Reflux | | | | | | | |
| 0.999 | 697 | 144 | 75 | 52 | 40 | 33 | 19 | 12 |
| 0.995 | 534 | 110 | 57 | 39 | 30 | 25 | 14 | 9 |
| 0.990 | 463 | 95 | 49 | 34 | 26 | 22 | 12 | 7 |
| 0.98 | 392 | 81 | 42 | 29 | 22 | 18 | 10 | 6 |
| 0.95 | 296 | 61 | 31 | 21 | 16 | 14 | 8 | 4 |
| 0.90 | 221 | 45 | 23 | 16 | 12 | 10 | 5 | 3 |

Ethyl acetate and ethanol boil only two degrees apart and have a relative volatility 1.16 which makes it impossible to separate them by conventional distillation or rectification. Table 2 shows that with an agent giving a relative volatility of 2, only 16 actual plates are required to get 99% purity.

TABLE 2

Theoretical and Actual Plates Required vs. Relative Volatility for Ethyl Acetate From Ethanol Separation

| Relative Volatility | Theoretical Plates Required At Total Reflux, 99% Purity | Actual Plates Required, /5% Efficiency |
|---|---|---|
| 1.5 | 23 | 31 |
| 1.8 | 17 | 23 |
| 2.0 | 12 | 16 |

OBJECTIVE OF THE INVENTION

The object of this invention is to provide a process or method of azeotropic distillation that will enhance the relative volatility of ethyl acetate and ethanol in their separation in a rectification column. It is a further object of this invention to identify effective azeotropic distillation agents that are stable and can he recycled.

SUMMARY OF THE INVENTION

The objects of this invention are provided by a process for the separation of ethyl acetate and ethanol which entails the use of certain organic compounds when employed as the agent in azeotropic distillation.

TABLE 3

Effective Azeotropic Distillation Agents For Separating Ethyl Acetate From Ethanol

| Compounds | Relative volatility |
|---|---|
| None | 1.16 |
| Methyl formate | 1.85 |
| 2,2-Dimethylbutane | 1.95 |
| Cyclohexane | 1.4 |
| Hexane | 1.6 |
| Cyclopentane | 1.85 |
| 2,2,4-Tri-methylpentane | 1.4 |
| Ethyl ether | 2.0 |
| t-Butyl methyl ether | 1.9 |
| Petroleum ether | 1.9 |
| Dimethoxymethane | 1.55 |
| 4-Methyl-2-pentanone | 1.4 |

DETAILED DESCRIPTION OF THE INVENTION

I have discovered that certain organic compounds will effectively increase the relative volatility between ethyl acetate and ethanol during rectification when employed as the agent in azeotropic distillation. They are, methyl formate, 2,2-dimethylbutane, cyclohexane, hexane, cyclopentane, 2,2,4-trimethylpentane, ethyl ether, t-butyl methyl ether, petroleum ether, dimethoxymethane and 4-methyl-2-pentanone.

THE USEFULNESS OF THE INVENTION

The usefulness of this invention can be demonstrated by referring to the data presented in Tables 1, 2 and 3. All of the successful agents show that ethyl acetate can be separated from ethanol by means of azeotropic distillation in a rectification column and that the ease of separation as measured by relative volatility is considerable.

WORKING EXAMPLE

1. Fifty grams of ethyl acetate —ethanol mixture and fifty grams of ethyl ether were charged to a vapor —liquid equilibrium still and refluxed for two hours. The vapor composition was 45.6% ethyl acetate and 54.4% ethanol. The liquid composition was 29.5% ethyl acetate and 70.5% ethanol. This is a relative volatility of 2.0.

I claim:

1. A method for recovering ethyl acetate from a mixture of ethyl acetate and ethanol which comprises distilling a mixture of ethyl acetate and ethanol in the presence of an azeotrope forming agent, recovering the ethyl acetate and the azeotrope forming agent as overhead product and obtaining the ethanol as bottoms product, wherein said azeotrope forming agent consists of one material selected from the group consisting of methyl formate, 2,2-dimethyl butane, hexane, cyclopentane, 2,2,4-trimethylpentane, t-butyl methyl ether, petroleum ether, dimethoxymethane and 4-methyl-2-pentanone.

* * * * *